United States Patent
Shiue et al.

(10) Patent No.: US 11,213,256 B2
(45) Date of Patent: Jan. 4, 2022

(54) BIOLOGICAL IMAGE PROCESSING METHOD AND BIOLOGICAL INFORMATION DETECTION DEVICE

(71) Applicant: FaceHeart Inc., Hsinchu (TW)

(72) Inventors: Tsuey-Huey Shiue, Hsinchu (TW); Chung-Shine Huang, Zhubei (TW); Kuan-Hung Chen, Hsinchu (TW); Po-Wei Huang, Douliu (TW); Da-Hong He, Taichung (TW); Chung-Han Lin, Taichung (TW)

(73) Assignee: FACEHEART INC., Hsinchu (TW)

( * ) Notice: Subject to any disclaimer, the term of this patent is extended or adjusted under 35 U.S.C. 154(b) by 68 days.

(21) Appl. No.: 16/733,022

(22) Filed: Jan. 2, 2020

(65) Prior Publication Data
US 2020/0330042 A1    Oct. 22, 2020

(30) Foreign Application Priority Data
Apr. 19, 2019    (TW) .................................. 108113890

(51) Int. Cl.
*G06T 5/00* (2006.01)
*A61B 5/00* (2006.01)
(Continued)

(52) U.S. Cl.
CPC ........ *A61B 5/7267* (2013.01); *A61B 5/02416* (2013.01); *A61B 5/7203* (2013.01);
(Continued)

(58) Field of Classification Search
CPC . A61B 5/7267; A61B 5/02416; A61B 5/7257; A61B 5/7203; A61B 5/0077;
(Continued)

(56) References Cited

U.S. PATENT DOCUMENTS

| | | | |
|---|---|---|---|
| 2010/0185064 A1* | 7/2010 | Bandic | A61B 5/415 600/306 |
| 2011/0301441 A1* | 12/2011 | Bandic | A61B 5/0059 600/306 |

(Continued)

FOREIGN PATENT DOCUMENTS

| | | |
|---|---|---|
| CN | 105960264 A | 9/2016 |
| EP | 2697771 A1 | 2/2014 |

(Continued)

*Primary Examiner* — Jose L Couso
(74) *Attorney, Agent, or Firm* — Birch, Stewart, Kolasch & Birch, LLP

(57) ABSTRACT

A biological image processing method is provided. The method acquires first time-frequency data from an image data; processing the first time-frequency data into the second time-frequency data using a filter module; and converting the second time-frequency data into a time domain signal. The filter module is obtained by machine learning, and is trained using a first sample time-frequency signal as input and a second sample time-frequency signal as output, wherein the noise of the time domain signal corresponding to the second sample time-frequency signal is less than the noise of the time domain signal corresponding to the first sample time-frequency signal. A biological information detection device is also provided.

24 Claims, 5 Drawing Sheets
(3 of 5 Drawing Sheet(s) Filed in Color)

(51) Int. Cl.
*G06T 7/00* (2017.01)
*A61B 5/024* (2006.01)

(52) U.S. Cl.
CPC ............ *A61B 5/7257* (2013.01); *G06T 5/002* (2013.01); *G06T 7/0012* (2013.01); *G06T 2207/10016* (2013.01); *G06T 2207/10024* (2013.01); *G06T 2207/20081* (2013.01); *G06T 2207/20084* (2013.01); *G06T 2207/30088* (2013.01); *G06T 2207/30201* (2013.01)

(58) Field of Classification Search
CPC ... A61B 5/0059; A61B 5/0082; A61B 5/0816; A61B 5/7282; A61B 5/721; A61B 5/18; A61B 5/0261; A61B 5/11; A61B 5/746; A61B 5/7845; A61B 5/441–445; A61B 5/01; A61B 5/163; A61B 5/165; A61B 5/0205; A61B 5/02405; A61B 5/0075; A61B 5/02055; A61B 5/168; A61B 5/08; A61B 5/0295; A61B 5/1032; A61B 5/1455; A61B 5/14551; A61B 5/14552; A61B 5/145; A61B 5/0022; A61B 5/02; A61B 5/021; A61B 5/024; A61B 2576/00; A61B 2503/22; A61B 3/112; A61B 1/0009; A61B 1/00186; A61B 1/0646; G06T 7/0012; G06T 7/0016; G06T 7/10; G06T 7/00; G06T 7/20; G06T 5/002; G06T 5/50; G06T 2207/20084; G06T 2207/20081; G06T 2207/20056; G06T 2207/10016; G06T 2207/10024; G06T 2207/30201; G06T 2207/30088; G06T 2207/30068; G06T 2207/30076; G06T 2207/20048; G06T 2207/30104; G06T 2207/30048; G06T 2207/20182; G06K 9/6256; G06K 9/46; G06K 9/4652; G06K 9/4661; G06K 9/6201; G06K 9/00845; G06K 9/3233; G06K 9/00255; G06K 9/00302; G06K 9/00906; G06K 2009/00939; G06K 2009/4666; G06N 3/0454; G06N 3/08–088; G16H 40/67; G16H 50/20; G16H 20/70; G16H 30/20; G16H 30/40; G16H 15/00; G06F 19/3418; G06F 19/3481; G06F 19/00; B60W 2040/0872; B60W 2040/0818; B60W 2540/22; B60W 2540/221; B60W 40/08

See application file for complete search history.

(56) References Cited

U.S. PATENT DOCUMENTS

| | | | |
|---|---|---|---|
| 2012/0150387 A1* | 6/2012 | Watson | A61B 5/0077 701/36 |
| 2012/0321759 A1* | 12/2012 | Marinkovich | G01J 3/508 426/231 |
| 2014/0275854 A1* | 9/2014 | Venkatraman | A61B 5/318 600/301 |
| 2017/0032522 A1* | 2/2017 | Quellec | G06T 7/0016 |
| 2019/0046056 A1* | 2/2019 | Khachaturian | A61B 5/02416 |
| 2019/0108447 A1* | 4/2019 | Kounavis | G06K 9/00355 |
| 2019/0287248 A1* | 9/2019 | Abe | G16H 50/30 |
| 2019/0313907 A1* | 10/2019 | Khachaturian | A61B 5/02416 |
| 2019/0320875 A1* | 10/2019 | Jones | A61B 5/1459 |
| 2019/0385288 A1* | 12/2019 | Stewart | G06T 5/002 |
| 2021/0052228 A1* | 2/2021 | Abe | A61B 5/7257 |

FOREIGN PATENT DOCUMENTS

| | | |
|---|---|---|
| WO | WO 2012/140531 A1 | 10/2012 |
| WO | WO 2015/117828 A1 | 8/2015 |
| WO | WO 2015/180986 A1 | 12/2015 |

* cited by examiner

BIOLOGICAL IMAGE PROCESSING METHOD AND BIOLOGICAL INFORMATION DETECTION DEVICE

BACKGROUND

Technical Field

The present invention relates to a data processing method and a detection device, and particularly relates to a biological diffusion image processing method and a detection device for detecting biological information through image.

Related Art

With the increasing popularity of the electronic devices having camera functions such as desktop computers, notebook computers, tablet computers, and smart phones, application programs that provides various functions are also constantly improving. Among them, the detection of biological information is one of the important ones.

Through capturing the dynamic image of a living organism, the electronic device can calculate various physiological information according to the frequency of changes in the dynamic image with respect to the image of the living organism. Physiological information, including heart rate, breathing, blood oxygen, etc., can be obtained from dynamic image. However, in the process of capturing dynamic image, the shaking of the living organism and the transformation of the environment lighting and the like all affect the quality of the dynamic image, and therefore noise might be generated in the process of extracting physiological information. Accordingly, how to effectively reduce the noise of physiological information obtained from dynamic images is one of the problems that need to be solved at present.

SUMMARY

The present invention provides an image processing method, which can improve a signal-to-noise ratio of the image corresponding to the biological information in the image data with the biological signal.

The image processing method provided by the present invention may be applied to a home care system and an in-vehicle driver monitoring system to reduce the signal-to-noise ratio of biological information in the image, thereby providing accurate physiological condition monitoring.

The biological image processing method of the present invention comprises: obtaining image data including a biological diffusion image; determining an observation area in the image data, wherein at least part of the biological diffusion image is located in the observation area; obtaining at least a first diffusion change data according to the change of the biological diffusion image in the observation area over time; inputting the first diffusion change data, performing frequency domain conversion and obtaining first time-frequency data; processing the first time-frequency data with the filter module, so as to obtain the second time-frequency data; performing inverse frequency domain conversion for the second time-frequency data, so as to obtain second diffusion change data. The filter module is obtained by machine learning, and is trained by inputting the first sample time-frequency data and outputting the second sample time-frequency data as the target, wherein the first sample time-frequency data corresponds to first sample diffusion change data of a sample biological image from the sample observation area of a sample image, the second sample time-frequency data corresponds to the second sample diffusion change data, and the noise of the second sample diffusion change data is less than the noise of the first sample diffusion change data.

The physiological information detection device of the present invention comprises an image capturing unit, a storage unit and a processing unit. The processing unit is electrically connected to the image capturing unit and the storage unit, and the processing unit comprises a main signal capturing module. The image capturing unit is configured to capture image data including biological diffusion image, and the storage unit stores the filter module. The above filter module is obtained by machine learning, and is trained by inputting the first sample time-frequency data and outputting the second sample time-frequency data as the target, wherein the first sample time-frequency data corresponds to first sample diffusion image change data of a sample biological image from the sample observation area of a sample image, the second sample time-frequency data corresponds to the second sample diffusion change data, and the noise of the second sample diffusion change data is less than the noise of the first sample diffusion change data. The processing unit determines an observation area in the image data, and at least a portion of the biological diffusion image is located in the observation area. The main signal capturing module obtains at least a first diffusion change data according to the change of the biological diffusion image in the observation area over time. The processing unit performs frequency domain conversion on the first diffusion change data as input and obtains the first time-frequency data, and processes the first time-frequency data with the filter module to obtain the second time-frequency data. The processing unit performs inverse frequency domain conversion on the second time-frequency data and obtains second diffusion change data.

In an embodiment of the invention, the above image processing method calculates physiological information of the living organism from the second diffusion change data.

In an embodiment of the invention, the above image data includes a plurality of image frames. Each image frame is composed of a plurality of pixel data, and each pixel data includes a plurality of color values. The first diffusion change data includes a plurality of grayscale values, each grayscale value is the combination of the color values of at least one pixel data of one image frame of the biological diffusion image in the observation area.

In an embodiment of the invention, the above image data is taken from a living organism, the biological diffusion image corresponds to a skin image of the living organism. In the first diffusion change data, each grayscale value includes a photoplethysmogram value, each photoplethysmogram value is obtained from a part of these pixel data from one of the image frames, and part of the pixel data corresponds to the skin image of the image frame in the observation area.

In an embodiment of the invention, the above image data is taken from a living organism. The image data includes a plurality of image frames, the biological diffusion image in the observation area corresponds to a facial image of the living organism in each image frame. Performing the frequency domain conversion to obtain the first time-frequency data further includes inputting the first position change data. The first position change data corresponds to the change of the position in the observation area over time, the first image change data includes a plurality of displacement data, and each of the displacement data refers the difference between the position in the observation area for one image frame and the position in the observation area for the previous image frame.

In an embodiment of the invention, the above image data is taken from a living organism. The image data includes a plurality of image frames, the observation area corresponds to the biological diffusion image for each image frame. Performing the frequency domain conversion to obtain the first time-frequency data further includes inputting the first background change data. The first background change data includes a plurality of background data, each background data refers the brightness of a portion of the image apart from the biological diffusion image in one of the image frames.

In an embodiment of the invention, the above first time-frequency data includes a plurality of frequency groups arranged along time. The first image change data acquires these frequency groups via short-time Fourier transform.

In an embodiment of the invention, the above first time-frequency data, the above second time-frequency data are two-dimensional data arranged along time and frequency domains.

In an embodiment of the invention, the above filter module is obtained through deep learning.

In an embodiment of the invention, the deep learning is employed at Convolutional Neural Network (CNN), a Recurrent Neural Networks (RNN), an Reinforcement Learning (RL), or Long Short-Term Memory (LSTM).

In an embodiment of the invention, the above second sample time-frequency data is obtained by a contact type heartbeat sensing device.

Based on the above, the biological image processing method and the biological information detection device of the present invention can process the first time-frequency data obtained from the image data by the filter modules, and can improve signal-to-noise ratio of the image data corresponding to the processed time-frequency data.

BRIEF DESCRIPTION OF THE DRAWINGS

The patent or application file contains at least one color drawing. Copies of this patent or patent application publication with color drawing will be provided by the USPTO upon request and payment of the necessary fee.

DETAILED DESCRIPTION

The image processing method provided by the present invention can be applied to electronic devices having abilities to capture image and process data, such as a server, a client, a desktop computer, a notebook computer, a network computer, a workstation, a Personal Digital Assistant (PDA), a tablet computer, or a smart phone, and the present invention is not limited to said applied type of electronic devices. Specifically, the image processing method provided by the present invention can be applied to the above electronic devices, wherein the diffusion data is, for example, a user's skin image from the observation area. That is, the image data formed of the light diffused by the user's skin.

It should be understood that although terms such as "first" and "second" in this specification may be used for describing various elements, components, data, or parts, the elements, components, data, or parts are not limited by such terms. The terms are only used to distinguish one element, component, data, or part. Therefore, such as the "the first element", "the first component", "the first data", or "the first part" described below may also be referred to as "the second element", "the second component", "the second data", or "the second part" without departing from the teachings of this specification.

Figure 1A:
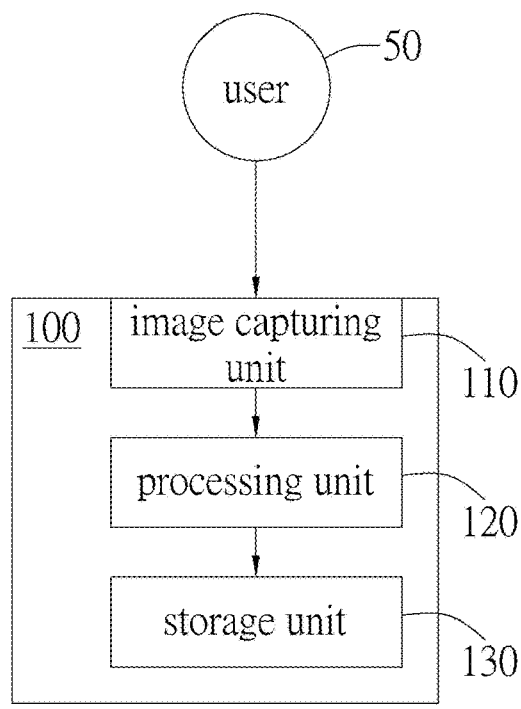
FIG. 1A is a schematic diagram of a physiological information detection device according to a first embodiment of the present invention.

FIG. 1A is a schematic diagram of a physiological information detection device of a first embodiment of the present invention. Referring to FIG. 1A, in the first embodiment of the present invention, the physiological information detection device 100 includes an image capturing unit 110, a processing unit 120, and a storage unit 130. The processing unit 120 is electrically connected to the image capturing unit 110 and the storage unit 130. The image capturing unit 110 is, for example, a photosensitive element such as a Charged-Couple Device (CCD) or a Complementary Metal-Oxide-Semiconductor (CMOS).

The function of the processing unit 120 in this embodiment can be implemented by, for example, a programmable unit such as a central processing unit (CPU), a microprocessor, a microcontroller, a digital signal processing (DSP) chip, and a field Programmable Gate Array (FPGA). The function of the processing unit 120 can also be implemented by an independent electronic device or an integrated circuit (IC).

The storage unit 130 of this embodiment may be any type of fixed or removable random access memory (RAM), read-only memory (ROM), flash memory or similar elements or a combination of the above elements.

The embodiments of the elements in the physiological information capturing device applied for the image processing method provided by the present invention are exemplified and described above. However, the present invention is not limited thereto. Hereinafter, an image processing method and a physiological information capturing device using the same provided by the present invention will be exemplified and described with reference to the above elements.

Figure 1B:
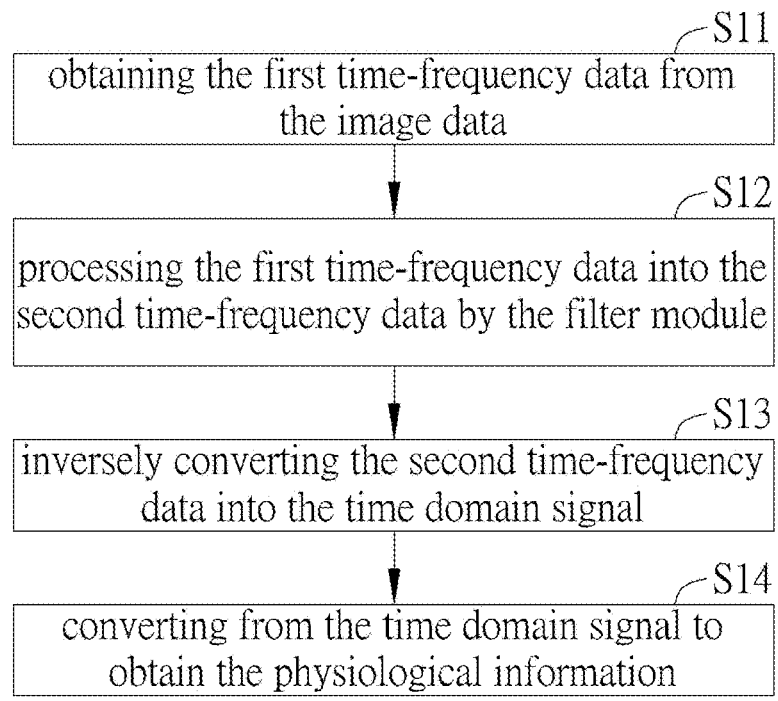
FIG. 1B is a schematic flow chart of an image processing method according to a first embodiment of the present invention.

Please refer to the schematic flow chart of the image processing method of the first embodiment of the present invention in FIG. 1B. The image processing method provided by the embodiment of the present invention converts the signals from the image data into frequency distributions according to different time period and then arranges them into first time-frequency data (step S11), wherein the signals from the image data is the signal changed over time, and this signal may include, for example, diffusion change data, position change data, or background change data. Then, the filter module processes part of the frequencies or reduces the intensity of part of the frequencies as the second time-frequency data (step S12), so that the processed second time-frequency signal can be inversely converted into time domain signal with lower noise (step S13). Since the signal processed by the above filter module contains less signal or noise apart from the physiological information, the physiological signal with improved signal-to-noise ratio can be obtained when the physiological signal is converted from the time domain signal (step S14). Specifically, the image processing method of the embodiment provides a noise filtering method, and the filter module used for filtering uses the time-frequency signal as the processing target. The filter module can filter out the frequencies of the noise in the time-frequency signal, so as to obtain the signal with improved signal-to-noise ratio. Embodiments of the present invention are described in detail below.

The image capturing unit 110 of the present embodiment is configured to capture image data from a living organism. Here, a user 50 is taken as an example. The image capturing area of the image capturing unit 110 includes the skin of the user 50, preferably the facial area of the user 50 or other areas having plentiful microvascular distribution. In other words, the image captured by the image capturing unit 110 is partially a biological diffusion image formed by the light diffused by the user 50. The image data is a dynamic image data, which includes a plurality of image frames or data representing changes of a plurality of pixels over time, and the present invention is not limited to the type of image data.

The image processing method provided by the present embodiment acquires time-frequency data from the above-described image data. Hereinafter, the acquisition procedure of the time-frequency data of the present embodiment will be exemplified and described. However, the present invention is not limited to the acquisition method for the time-frequency data described herein.

After the image capturing unit 110 of the embodiment obtains the image data, the processing unit 120 acquires the image data from the image capturing unit 110, and determines the observation area in the image data. The above observation area is an area of the image data corresponding to the biological diffusion image at each time point. In this embodiment, the observation area corresponds to the area of the image data corresponding to the image of the user 50, and the observation area corresponds to the area containing the skin image of the user 50, preferably including the area of the facial image of the user 50, or any other portion of user that is suitable for observing the change of the amount of light absorption due to changes in blood flow, but the present invention is not limited thereto.

After the observation area of the present embodiment is determined, the processing unit 120 obtains a first diffusion change data according to a change of a part of the image data in the observation area over time. For example, the first diffusion change data corresponds to a change in the color value of the pixel over time, but the present invention is not limited thereto.

Here, the first diffusion change data is taken as an example. After the processing unit 120 of the present embodiment obtains the first diffusion change data, the processing unit 120 performs frequency domain conversion on the first diffusion change data. The frequency domain conversion is, for example, conversion of the value in the obtained first diffusion change data from a time domain to a frequency domain. Preferably, the frequency domain conversion in this embodiment converts the first diffusion change data in different time intervals into the frequency domain, so as to obtain a plurality of frequency distribution data in different time intervals, thereby forming first time-frequency data.

The storage unit 130 of the present embodiment stores a filter module, and the filter module is obtained by machine learning. Specifically, the filter module stored in the storage unit 130 of the present embodiment is obtained by machine learning in advance, and is trained by inputting the first sample time-frequency data and outputting the second sample time-frequency data. The first sample time-frequency data is obtained, for example, from a sample biological image in a sample observation area of a sample image. For example, the sample image is obtained from the image data of the living organism, and the second sample time-frequency data is the sample data obtained in different manner from the above living organism. The stated sample image and the stated sample data have the same physiological information, and the noise of the stated sample data is lower than the noise of the stated image data. By machine learning, the filter module can figure out the relationship between the first sample time-frequency data with higher noise and the second sample time-frequency data with lower noise, such as the frequency range in which the noise occurs, and therefore can further provide the effect of reducing noise for other time-frequency data.

In other words, the first sample time-frequency data and the second sample time-frequency data can be converted into the first sample diffusion change data and the second sample diffusion change data in the time domain by the inverse frequency domain conversion, and the second sample diffusion change data has a higher signal-to-noise ratio than the first sample diffusion change data. For example, the second sample diffusion change data can be obtained from the living organism through a contact type heartbeat sensing device, and the first sample diffusion change data can be obtained through the image, but the present invention is not limited thereto. By machine learning, the filter module can figure out parameters, layers, weights, etc. that can improve the signal-to-noise ratio of other time-frequency data based on the relationship between the first sample time-frequency data and the second sample time-frequency data. Thus, the first sample change data obtained from the image can be processed into signal having the signal-to-noise ratio similar to that of the signal provided by the contact type sensing device.

After the processing unit 120 of the present embodiment obtains the first time-frequency data, the processing unit 120 acquires the filter module from the storage unit 130, so as to process the first time-frequency data to obtain the second time-frequency data. Since the filter module is trained and obtained by the above first sample time-frequency data and the above second sample time-frequency data. Therefore, the second time-frequency data obtained after the processing can be more suitable for the requirement. For example, the stated requirement is that a second pixel change data can be obtained through the inverse frequency domain conversion of the second time-frequency data, and the noise in the second pixel change data is lower than the noise in the first pixel change data.

With the above filter module, the image processing method provided by the present invention can filter out noise in image processing, so as to provide improved signal quality. Since the filter module after training can determine which signals of frequency bands or which part of signals in the time-frequency signal is noise, the signals can be filtered out so that the inverse converted signal can have better signal quality.

Specifically, the image processing method of the above embodiment may, for example, calculate the physiological information of the living organism (that is, the user 50) from the second diffusion change data after acquiring the second diffusion change data. The value change frequency in the second diffusion change data corresponds to the image change frequency in the image data, and such frequency possesses the physiological information of the user 50. Meanwhile, though the filtering effect of the filter module, the second diffusion change data has less noise apart from the frequency data corresponding to the physiological information of the user 50, so that the accuracy of the physiological signal can be improved. Preferably, the second diffusion change data has, for example, frequency data corresponding to physiological information of the user 50. For example, the physiological information described above might be the heartbeat frequency, heart rate variability (HRV), blood pressure, breathing, etc., of the user 50, but the present invention is not limited thereto.

Figure 2A:
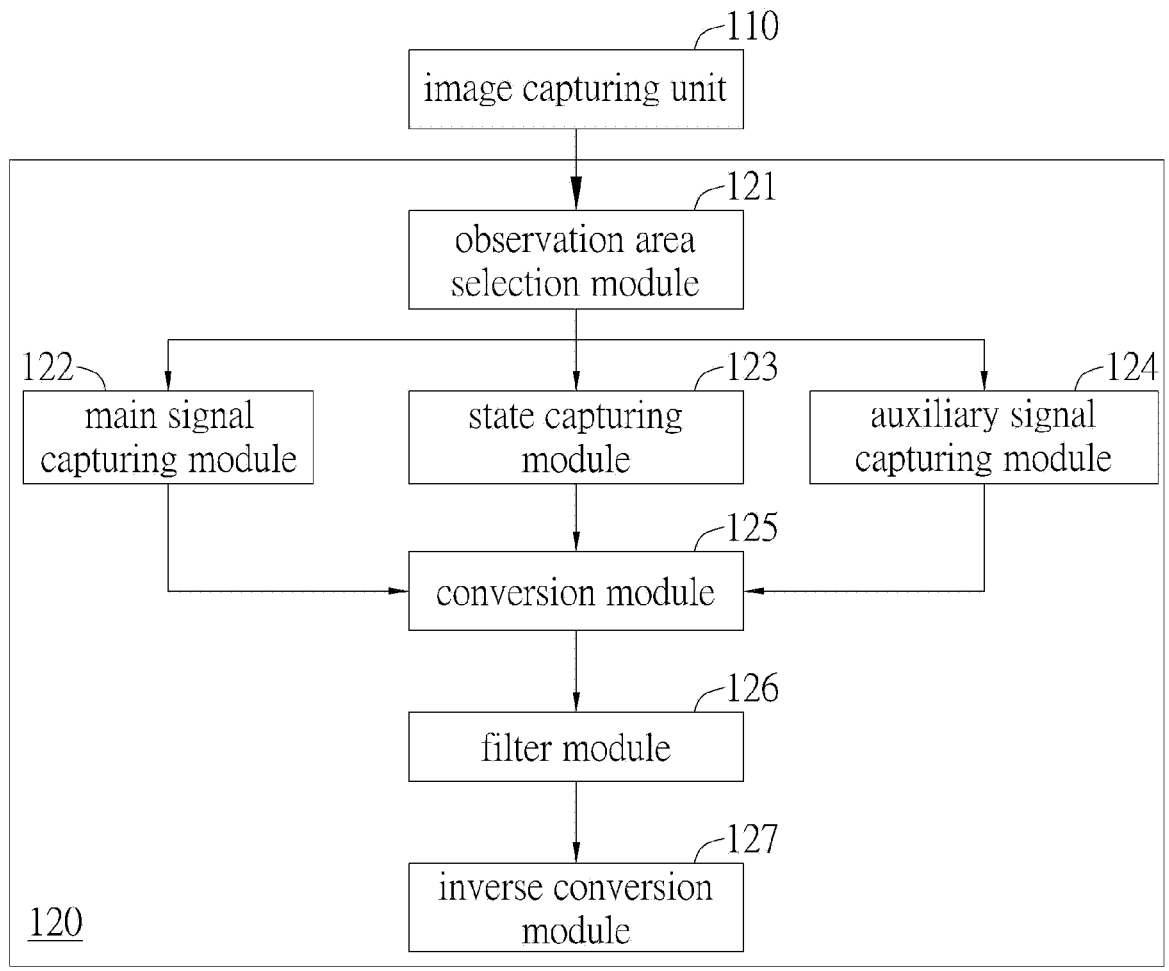
FIG. 2A is a schematic diagram of an image capturing unit and a processing unit according to a first embodiment of the present invention.
Figure 2B:
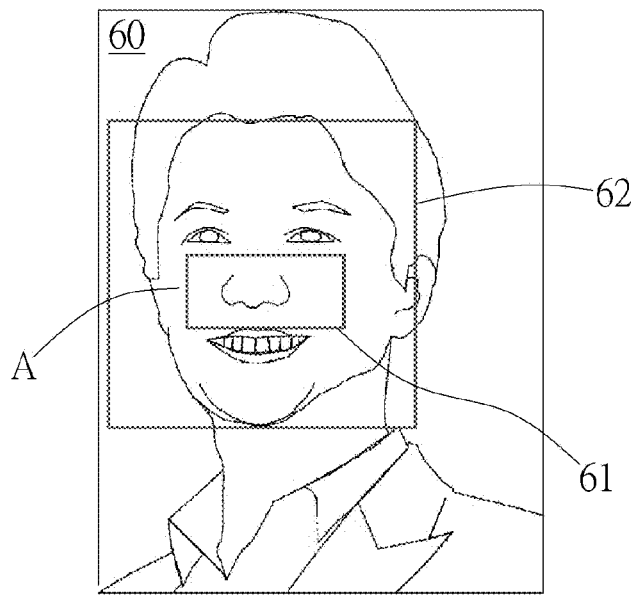
FIG. 2B is a schematic diagram of image frame according to a first embodiment of the present invention.

The image processing method of this embodiment can be used to determine an observation area in the image data, preferably an area containing the skin of the living organism. Referring to the image capturing unit and the processing unit shown in FIG. 2A, the processing unit 120 of the present embodiment includes an observation area selection module 121. The observation area selection module 121 is configured to determine the position of the observation area in the image data, preferably an area including the facial image. Referring to FIG. 2B, the above observation area selection module 121 is configured to determine the position of the facial image 61 in the image frame 60, and preferably, the position of the background image 62 is also determined. Since the human face has plentiful microvascular distribution, when the observation area A is set as the area including the facial image, the processing unit 120 can readily obtain the first diffusion change data from small changes in the image.

The type of input data for frequency domain conversion will be further explained below. It should be particularly noted that the following input for frequency domain conversion in the present embodiment is a combination including various embodiments and aspects, and the present invention is not limited to the combination of these embodiments and aspects. In other embodiments, when applying the image processing method provided by the present invention, a person having ordinary skill in the art may also select single change data or a combination of kinds of change data.

The processing unit 120 of the present embodiment obtains a plurality of grayscale value signals with respect to the image data. Referring to FIG. 2A, in the first embodiment of the present invention, the processing unit 120 includes a main signal capturing module 122 for capturing the original image signal of the image data from the image capturing unit 110. In detail, the image data of the present embodiment includes a plurality of image frames, and each image frame is composed of a plurality of pixel data. The above pixel data is, for example, a value of three primary colors forming a pixel, and each pixel data includes a plurality of color values. The grayscale value capturing module 122 of the present embodiment multiplies the color values in at least part of the pixel data located in the observation area A in each image frame by the respective weights and then combines them to obtain the grayscale values. For example, the grayscale value may be R*0.229+G*0.587+B*0.114, where R is a red value; G is a green value; B is a blue value. The above red value, green value, or blue value corresponds to the brightness of each color in the display signal or the transparency of the light valve. However, the present invention is not limited to the weights of these color values described above. In other embodiments, the color values may be any values used to represent the luminance values of the three primary colors in various image formats, or may be other numerals, other values that is suitable for representing the combination of the color for an appropriate color space. On the other hand, the grayscale value referred in this embodiment is not limited to the linear combination described above, and is not limited to any grayscale parameters used in other fields. The grayscale values provided by the present invention may include photoplethysmogram values obtained by combining the above color values in other embodiments, and the embodiments will be further described below.

Heartbeat and respiration of the living organisms can cause changes in blood flow of the microvessels adjacent to the skin, which therefore affects the rate that the skin absorbs external light. Thus, when recording the grayscale values over time, the change frequency of heart rhythm and respiration of the living organisms are also recorded by the grayscale values. Preferably, the grayscale value may further include photoplethysmogram value, and the photoplethysmogram value of these grayscale value may correspond to the volume of blood under the skin of the living organisms, thereby values such as heart rhythm, blood pressure, and flow direction can be calculated and estimated.

Specifically, the processing unit 120 of the present embodiment may further obtain photoplethysmogram value changed over time with respect to the image located in the observation area in the image data. In detail, the processing unit 120 may also obtain these photoplethysmogram value in the image frames in the image data through the main signal capture module 122. For example, the above photoplethysmogram value may be obtained by remote Photoplethysmography (rPPG), and the state of blood perfusion into the dermis and subcutaneous tissue can be detected by measuring the change amount of light absorption. The method for obtaining the above photoplethysmogram value preferably includes chrominance (CHROM), plane orthogonal to the skin (POS) or Green Red Difference Method (GRD), but the invention is not limited thereto.

The processing unit 120 of the present embodiment may further obtain the first image change data with respect to the change of the observation area in the image data. In detail, the processing unit 120 further includes a state capturing module 123 for detecting the position of the observation area A in each image frame 60. The processing unit 120 further includes an auxiliary signal capturing module 124 for detecting the brightness of each background image 62 outside the observation area A. In other embodiments, the observation area in the image frame of the image data may contain both a part of the facial image and a part of the background image, and the brightness of the background image 62 may be obtained in the observation area, but the present invention is not limited thereto.

The signal used as the input for the frequency domain conversion includes a plurality displacement data changed over time and a plurality of background data. The displacement data represents a difference between the position of the observation area in each image frame and the position of the observation area in the previous image frame. That is, the change amount of the position of the observation area over time in each image frame. The background data represents the brightness value of the background image in each image frame. That is, it is the change amount of the ambient light around the living organisms, that is, the part of image apart from the biological diffusion image. In other embodiments, the processing unit may include only the state capturing module or the auxiliary signal capturing module. That is, the first image change data may include only the displacement data or the background data, but the present invention is not limited thereto.

It can be seen from the above that the processing unit 120 of the present embodiment can obtain grayscale values, photoplethysmogram value, displacement data or background data changed over time from the image data, and input the above values or data for frequency domain conversion. Since the first diffusion change data changes over time, the processing unit 120 performs time-frequency conversion on the input data described above. In detail, the processing unit 120 includes, for example, a conversion module 125, and the conversion module 125 can analyze the change frequency of the values in the input data and the distribution intensity of each frequency. Specifically, the conversion module 125 can perform short-time Fourier transform on the input data described above to obtain the first time-frequency data. The first time-frequency data includes a plurality of frequency groups arranged along time, and the input data acquires these frequency groups via a short-time Fourier transform.

Please refer to the schematic diagram of the time-frequency data shown in FIGS. 3A-3D. For example, in the first time-frequency data, a horizontal axis can be a timeline, and a vertical axis can be a two-dimensional data of a frequency distribution. According to the first image change data of each time interval, each vertical axis can represent the state of the frequency distribution of the first image change data in this time interval.

Referring to FIG. 2A, in this embodiment, after the first image change data is converted into the first time-frequency data by the conversion module 125, the first time-frequency data can be processed into the second time-frequency data via the filter module 126. As described above, the filter module 126 is obtained through machine learning of the first sample time-frequency data and the second sample time-frequency data, and it can filter out the frequency corresponding to the noise in the first time-frequency data.

After the processing unit 120 of the present embodiment processes the first time-frequency signal into the second time-frequency signal, the second time-frequency signal is converted into a time-domain signal by inverse conversion, that is, the second image change data. In detail, the processing unit 120 of the present embodiment further includes an inverse conversion module 127. The inverse conversion module 127 is configured to convert the time-frequency signal into a time domain signal. Since the second time-frequency signal processed by the filter module 126 contains lower noise, the second image change data with lower noise can be obtained after being converted by the inverse conversion module 127. In other words, for example, when the first image change data contains a heartbeat change frequency corresponding to the user 50, the second image change data can more clearly present the heartbeat change frequency.

In other aspects, the filter module 126 of the present embodiment is obtained by machine learning such as deep learning. Because the first time-frequency signal is a signal changed over time, the filter module 126 can be preferably trained and obtained by Recurrent Neural Networks (RNN), Reinforcement Learning (RL), or Long Short-Term Memory (LSTM) model, thereby providing suitable filtering effect. In further aspects, since the first time-frequency signal is a two-dimensional data and can be represented as a graphic, the filter module 126 can be trained and obtained by a Convolutional Neural Network (CNN). Preferably, the filter module 126 can be trained and obtained by the architecture of a self-encoded Multi-Convolutional Auto-Encoder (CAE), so as to provide a suitable filtering effect. The present invention is not limited to the above-described machine learning mode, and a person having ordinary skill in the art can adjust the method for machine learning as needed.

In other aspects, since the first image change data can be presented in a plurality of various formation, when the user applies the image processing method provided by the present invention, in the training for the filter module, multiple grayscale values, multiple photoplethysmogram value, multiple displacement data or multiple background data can all be input to train the filter module, or one of them or some of them can be input to train the filter module. It depends on the user's needs and the performance of the device. In other words, the image processing method proposed by the present invention can use multi-channel signals to train the filter model.

Figure 3A:
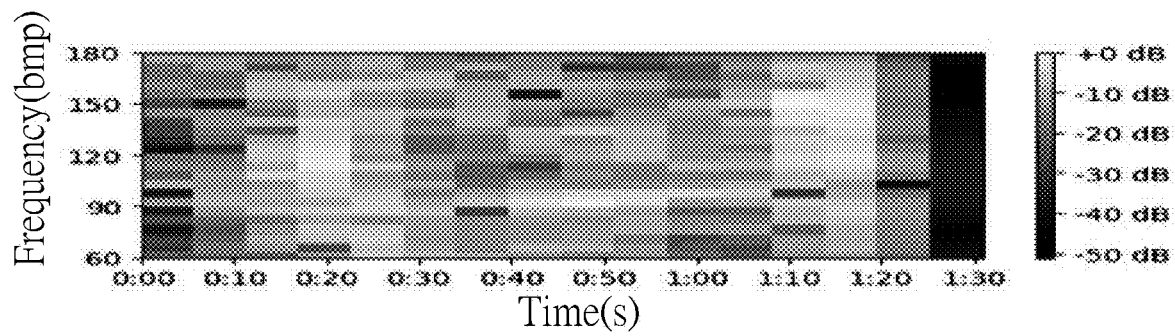
FIGS. 3A to 3D are a schematic diagram of time-frequency data according to an example of the present invention.
Figure 3B:
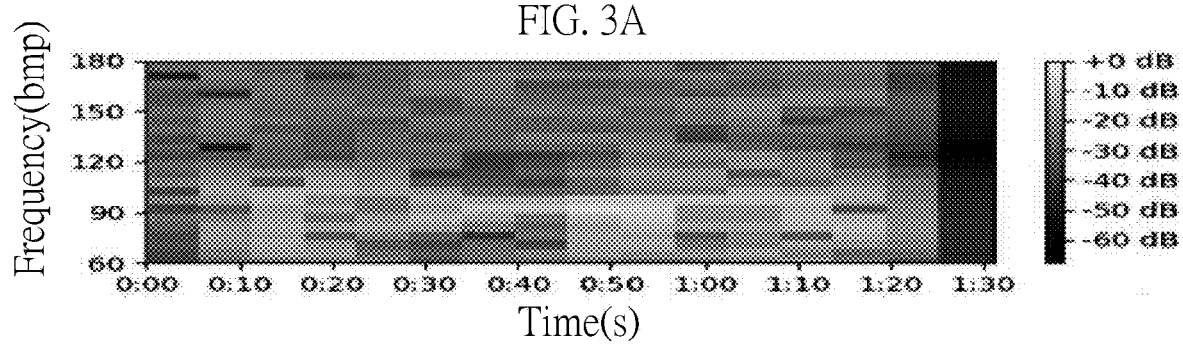
Figure 3C:
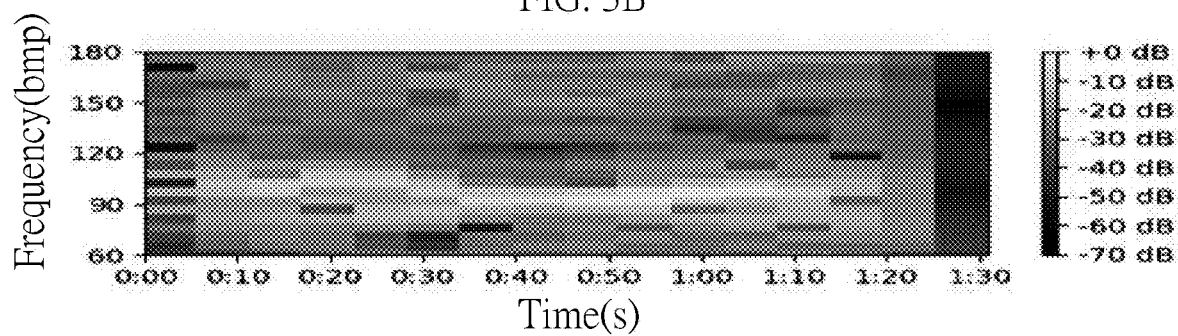
Figure 3D:
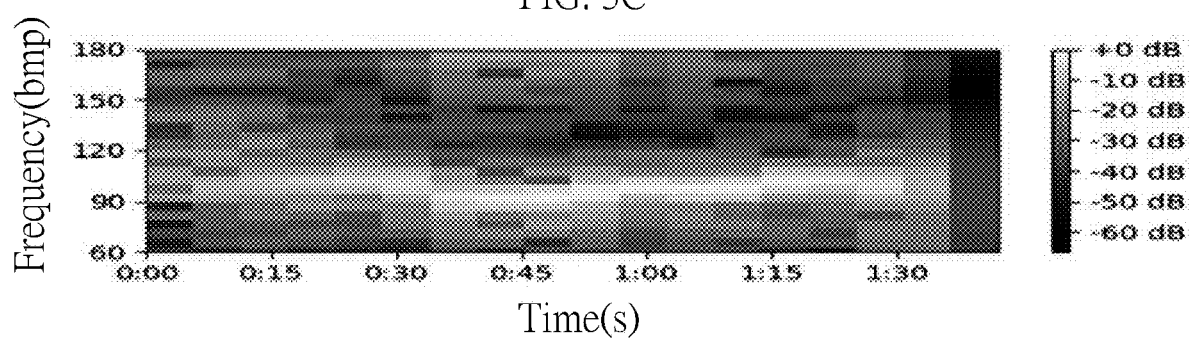
Figure 4A:
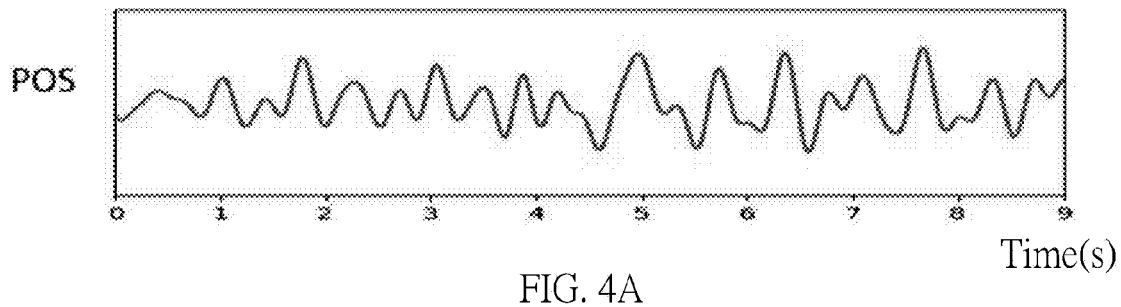
FIGS. 4A to 4D are schematic diagrams of image change data in an example of the present invention.
Figure 4B:
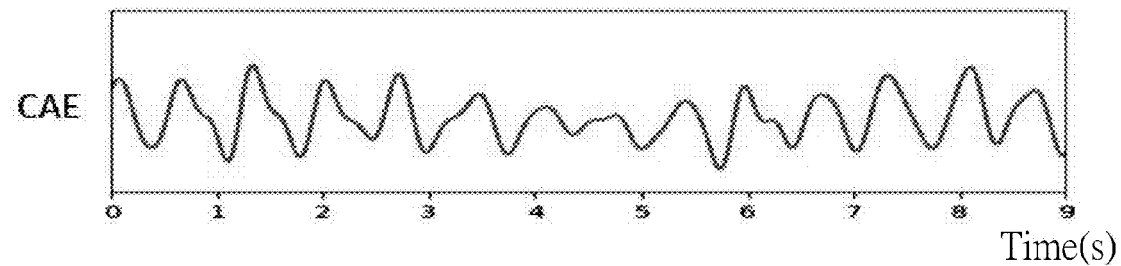
Figure 4C:
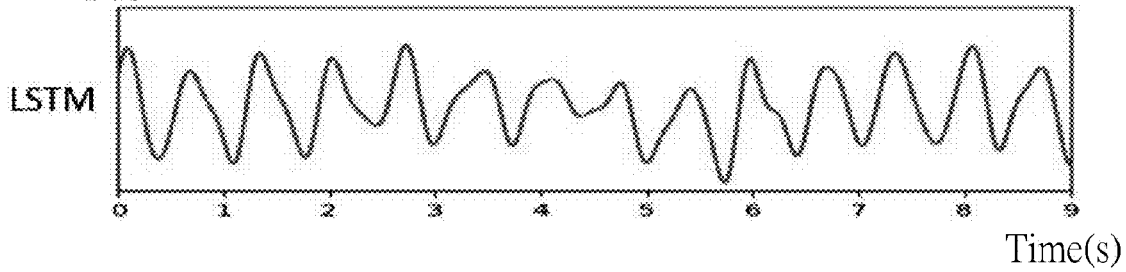
Figure 4D:
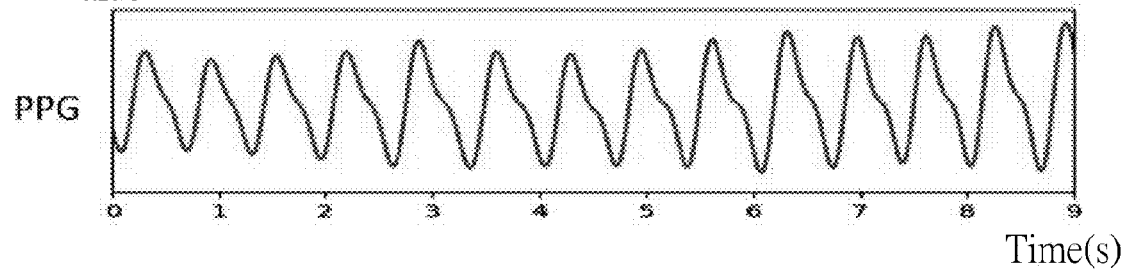

Several examples will be exemplified below to illustrate the effects of the method and the device provided by the present invention. Please refer to FIG. 3A to FIG. 3D and FIG. 4A to FIG. 4D, wherein FIG. 3A is an unprocessed first time-frequency data, which corresponds to the unprocessed first diffusion change data in FIG. 4A, and photoplethysmogram value is taken as an example; FIG. 3B is a second time-frequency data processed by a filter module trained by a self-encoded Multi-Convolutional Auto-Encoder, which corresponds to the second diffusion change data processed in FIG. 4B; FIG. 3C is a second time-frequency data processed by the filter module trained through the long-term and short-term memory training model, which corresponds to the second diffusion change data processed in FIG. 4C; FIG. 3D is the time-frequency data measured by a contact type sensing device, which corresponds to the diffusion change data in FIG. 4D. As can be seen from FIG. 3A to FIG. 3D, and FIG. 4A to FIG. 4D, both the filter module trained via Convolutional Auto-Encoder or the filter module trained via the long-term and short-term memory training model can provide suitable noise filtering effects. Therefore, a diffusion change signal with improved signal-to-noise ratio can be provided to provide more accurate physiological information such as heart rhythm, heart rate variability, and respiration.

Figure 5:
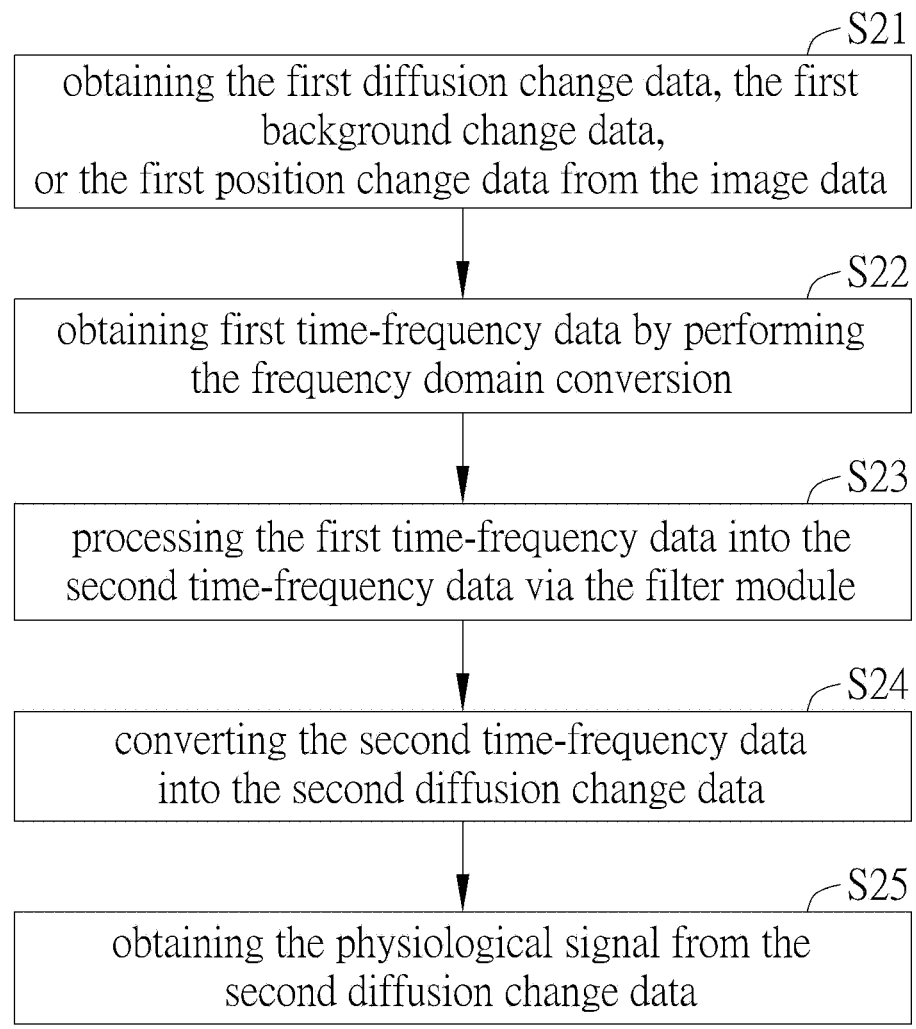
FIG. 5 is a schematic flow chart of an image processing method according to an embodiment of the present invention.

FIG. 5 is a schematic flow chart of an image processing method according to an embodiment of the present invention. In detail, the image processing method of the present invention can obtain image data by the imaging capturing device in an optical manner without contacting the user, and obtain the first diffusion change data, the first background change data, or the first position change data in the image data (step S21). It is preferable to obtain all the three kinds of materials to further ensure accuracy. The first diffusion change data may include photoplethysmogram value changed over time, the first position change data may include an observation area displacement value, and the first background change data may include a background light and shade change value. The first time-frequency data can be obtained by performing the short-time Fourier transform on the above data (step S22). The first time-frequency data is processed into the second time-frequency data via the filter module (step S23), and the filter module removes the frequency corresponding to the noise in the first time-frequency data based on the experience of the previous sample time-frequency signal. The second time-frequency data is converted into the second image change data through the inverse frequency domain conversion (step S24), wherein the second image change data and the first image change data are both the time domain signal. Next, the physiological signal is calculated from the second image change data (step S25).

Through the filter module described above, the biological information detection device and the biological image processing method thereof provided by the present invention can effectively obtain physiological signals with low noise, and can be used to monitor the health status of members in need of care at hospitals, wards, or even home. Meanwhile, high quality of function for observation and determination of physiological signals such as heart rhythm can be ensured, so as to reduce the possibility of misjudgment of physiological signals. In other aspects, for example, in a system such as a vehicle, the biological detection device and the biological image processing method thereof provided by the present invention can be used to monitor the health status of the driver effectively. Thus, a warning can be raised when the driver discomfort, shock, or abnormally high or low heart rate occurs, and it might even notify the car to slow down to avoid accidents.

In sum, the biological image processing method provided by the present invention converts the first image change data from the image data into a time-frequency signal, and then filters the time-frequency signal by a filter module, wherein the filter module is previously trained with the sample time domain signal. Therefore, the image processing method can provide a superior noise filtering function, and the physiological information detection device applying the method can also provide an accurate physiological information detection effect.

REFERENCE NUMERALS

A: Observation area
S11-S14: Step
S21-S25: Step
50: User
60: Image frame
61: Facial image
62: Background image
100: Physiological information detection device
110: Image capturing unit
120: Processing unit
121: Observation area selection module
122: Main signal capturing module
123: State capturing module
124: Auxiliary signal capturing module
125: Conversion module
126: Filter module
127: Inverse conversion module
130: Storage unit

What is claimed is:

1. A biological image processing method, comprising:
   obtaining image data including a biological diffusion image;
   determining an observation area in the image data, wherein at least part of the biological diffusion image is located in the observation area;
   obtaining at least a first diffusion change data according to the change of the biological diffusion image in the observation area over time;
   inputting the first diffusion change data, performing frequency domain conversion and obtaining first time-frequency data;
   processing the first time-frequency data with a filter module, so as to obtain second time-frequency data; and
   performing inverse frequency domain conversion on the second time-frequency data, so as to obtain second diffusion change data;
   wherein the filter module is obtained by machine learning, and is trained by inputting first sample time-frequency data and outputting second sample time-frequency data as the target, and
   wherein the first sample time-frequency data corresponds to a first sample diffusion change data of a sample biological image from a sample observation area of a sample image, the second sample time-frequency data corresponds to a second sample diffusion change data, and
   wherein the noise of the second sample diffusion change data is less than the noise of the first sample diffusion change data.

2. The biological image processing method according to claim 1, further comprising:
   calculating physiological information of a living organism from the second diffusion change data.

3. The biological image processing method according to claim 1, wherein the image data includes a plurality of image frames, each image frame is composed of a plurality of pixel data, and each pixel data includes a plurality of color values, and
   wherein the first diffusion change data includes a plurality of grayscale values, each grayscale value is the combination of the color values of at least one pixel data of one image frame of the biological diffusion image in the observation area.

4. The biological image processing method according to claim 3, wherein the image data is taken from a living organism, the biological diffusion image corresponds to a skin image of the living organism, and
   wherein, in the first diffusion change data, each grayscale value includes a photoplethysmogram value, each photoplethysmogram value is obtained from a part of these pixel data from one of the image frames, and part of the pixel data corresponds to the biological diffusion image of the image frame in the observation area.

5. The biological image processing method according to claim 1, wherein the image data is taken from a living organism, the image data includes a plurality of image frames, the biological diffusion image in the observation area corresponds to a facial image of the living organism in each image frame, and
   wherein, after the step of determining the observation area in the image data, the biological image processing method further includes:
   obtaining a first position change data according to the change of the position of the observation area over time, wherein the first position change data includes a plurality of displacement data, and each of the displacement data refers the difference between the position of the observation area for one image frame and the position of the observation area for the previous image frame;
   performing the frequency domain conversion to obtain the first time-frequency data further includes inputting the first position change data, wherein the first sample time-frequency signal also corresponds to a first sample position change data, and the first sample position change data corresponds to the change of the sample observation area in the sample image with time.

6. The biological image processing method according to claim 1, wherein the image data is taken from an living organism, the image data includes a plurality of image frames, and the observation area corresponds to the biological diffusion image in each of the image frames;

wherein, after the step of determining the observation area in the image data, the biological image processing method further includes:

obtaining a first background change data according to a part of the image data apart from the biological diffusion image, the first background change data includes a plurality of background data, each of the background data refers the brightness of a portion of the image apart from the biological diffusion image in one of the image frames;

performing the frequency domain conversion to obtain the first time-frequency data further includes inputting the first background change data, wherein the first sample time-frequency signal further corresponds to a first sample background change data, and the first sample background change data corresponds to a brightness of a portion of the image other than the sample biological image in the sample image.

7. The biological image processing method according to claim 1, wherein the first time-frequency data includes a plurality of frequency groups arranged along time, and the frequency domain conversion is a short-time Fourier transform.

8. The biological image processing method according to claim 7, wherein the first time-frequency data, the second time-frequency data are two-dimensional data arranged along time and frequency domains.

9. The biological image processing method according to claim 1, wherein the filter module is trained and obtained through deep learning.

10. The biological image processing method according to claim 9, wherein the deep learning is employed at Convolutional Neural Network (CNN), a Recurrent Neural Networks (RNN), a Reinforcement Learning (RL), or Long Short-Term Memory (LSTM).

11. The biological image processing method according to claim 1, wherein the sample biological image is an image formed of the light diffused by the sample living organism's skin.

12. The biological image processing method according to claim 1, wherein the second sample time-frequency data is obtained by a contact type heartbeat sensing device.

13. A physiological information detection device, comprising:

an image capturing unit, configured to capture image data including biological diffusion image;

a storage unit, storing a filter module, wherein the filter module is obtained by machine learning, and is trained by inputting first sample time-frequency data and outputting second sample time-frequency data as the target, and the first sample time-frequency data corresponds to first sample diffusion change data of a sample biological image from a sample observation area of a sample image, the second sample time-frequency data corresponds to second sample diffusion change data, and the noise of the second sample diffusion change data is less than the noise of the first sample diffusion change data; and a processing unit including a main signal capturing module, the processing unit electrically connected to the image capturing unit and the storage unit, wherein, the processing unit determines the observation area in the image data, and at least a portion of the biological diffusion image is located in the observation area;

the main signal capturing module obtains at least a first diffusion change data according to the change of the biological diffusion image in the observation area over time, the processing unit performs frequency domain conversion on the first diffusion change data as input and obtains first time-frequency data, and processes the first time-frequency data by the filter module to obtain the second time-frequency data; and the processing unit performs inverse frequency domain conversion on the second time-frequency data and obtains second diffusion change data.

14. The physiological information detection device according to claim 13, wherein the processing unit calculates physiological information of a living organism from the second diffusion change data.

15. The physiological information detection device according to claim 13, wherein the image data includes a plurality of image frames, each image frame is composed of a plurality of pixel data, and each pixel data includes a plurality of color values, and wherein the first diffusion change data includes a plurality of grayscale values, each grayscale value is the combination of the color values of at least one pixel data of one image frame of the biological diffusion image in the observation area.

16. The physiological information detection device according to claim 15, wherein the image capturing unit extracts the image data from a living organism, and the biological diffusion image corresponds to a skin image of the living organism, wherein, in the first diffusion change data, each grayscale value includes a photoplethysmogram value, each photoplethysmogram value is obtained from a part of these pixel data from one of the image frames, and part of the pixel data corresponds to the biological diffusion image of the image frame in the observation area.

17. The physiological information detection device according to claim 13, wherein the processing unit further includes:

a state capturing module, for obtaining first position change data from the observation area of the image data; wherein the image capturing unit extracts the image data from a living organism, the image data includes a plurality of image frames, and the biological diffusion image in the observation area corresponds to a facial image of the living organism in each of the image frames;

wherein the first position change data includes a plurality of displacement data, and each of the displacement data refers the difference between the position of the observation area for one image frame and the position of the observation area for the previous image frame;

and wherein performing the frequency domain conversion to obtain the first time-frequency data by the processing unit further includes inputting the first position change data, wherein the first sample time-frequency signal also corresponds to first sample position change data, and the first sample position change data corresponds to the change of the sample observation area in the sample image with time.

18. The physiological information detection device according to claim 13, wherein the processing unit further includes an auxiliary signal capturing module for obtaining a first background change data from an observation area of the image data, and wherein the image data is taken from a living organism, the image data includes a plurality of image frames, and the observation area corresponds to the biological diffusion image and a background image of the living organism in each of the image frames; and wherein the first background change data includes a plurality of background data, and each of the background data refers brightness of the background image in one of the image frames; wherein performing the frequency domain conversion to obtain the first time-frequency data by the processing unit further includes inputting the first background change data, the first sample time-frequency signal further corresponds to first sample background change data, and the first sample background change data corresponds to a brightness of a portion of the image other than the sample biological image in the sample image.

19. The physiological information detection device according to claim 13, wherein the first time-frequency data includes a plurality of frequency groups arranged along time, and the frequency domain conversion is a short-time Fourier transform.

20. The physiological information detection device according to claim 19, wherein the first time-frequency data, the second time-frequency data are two-dimensional data arranged along time and frequency domains.

21. The physiological information detection device according to claim 13, wherein the filter module is trained through deep learning and is stored in the storage unit.

22. The physiological information detection device according to claim 21, wherein the deep learning is employed at Convolutional Neural Network (CNN), a Recurrent Neural Networks (RNN), an Reinforcement Learning (RL), or Long Short-Term Memory (LSTM).

23. The physiological information detection device according to claim 13, wherein the sample biological image is an image formed of the light diffused by the sample living organism's skin.

24. The physiological information detection device according to claim 13, wherein the second sample time-frequency data is obtained by a contact type heartbeat sensing device.

* * * * *